United States Patent [19]

Hart

[11] Patent Number: 5,658,299

[45] Date of Patent: Aug. 19, 1997

[54] SURGICAL LIGATING DEVICE AND METHOD FOR USING SAME

[75] Inventor: Charles C. Hart, Huntington Beach, Calif.

[73] Assignee: Applied Medical Resources, Laguna Hills, Calif.

[21] Appl. No.: 504,912

[22] Filed: Jul. 20, 1995

[51] Int. Cl.[6] ............................................. A61B 17/10
[52] U.S. Cl. ................................. 606/139; 606/148
[58] Field of Search .................................. 606/110, 139, 606/148, 223, 144, 145, 147; 128/898

[56] References Cited

U.S. PATENT DOCUMENTS

| | | |
|---|---|---|
| 5,144,961 | 9/1992 | Chen et al. . |
| 5,196,022 | 3/1993 | Bilweis . |
| 5,211,650 | 5/1993 | Noda ................................ 606/139 |
| 5,281,238 | 1/1994 | Chin et al. . |
| 5,300,078 | 4/1994 | Buelna . |
| 5,312,423 | 5/1994 | Rosenbluth et al. ............... 606/148 |
| 5,320,629 | 6/1994 | Noda et al. ........................ 606/148 |
| 5,336,229 | 8/1994 | Noda .................................. 606/144 |
| 5,354,304 | 10/1994 | Allen et al. . |
| 5,405,354 | 4/1995 | Sarrett .............................. 606/148 |
| 5,431,666 | 7/1995 | Sauer et al. ....................... 606/139 |

Primary Examiner—Michael Powell Buiz
Assistant Examiner—Kevin Truong
Attorney, Agent, or Firm—Richard L. Myers

[57] ABSTRACT

A ligating device includes an elongate tube having an interior channel and an axis extending between a proximal end and a distal end. A handle is disposed at the proximal end of the tube. Distal portions of the tube define a recess extending into the channel transversely of the axis. A suture extending through the channel includes first portions disposed proximally of the recess and second portions disposed distally of the recess. An engagement apparatus movable by operation of the handle engages the suture distally of the recess and is operable to draw the suture (loop) into the tube. In this manner, the suture substantially encircles the conduit permitting ligation of the conduit. An associated method includes the steps of moving the engagement apparatus to engage the suture and withdraw the suture ends from the body after substantially encircling the body conduit.

24 Claims, 9 Drawing Sheets

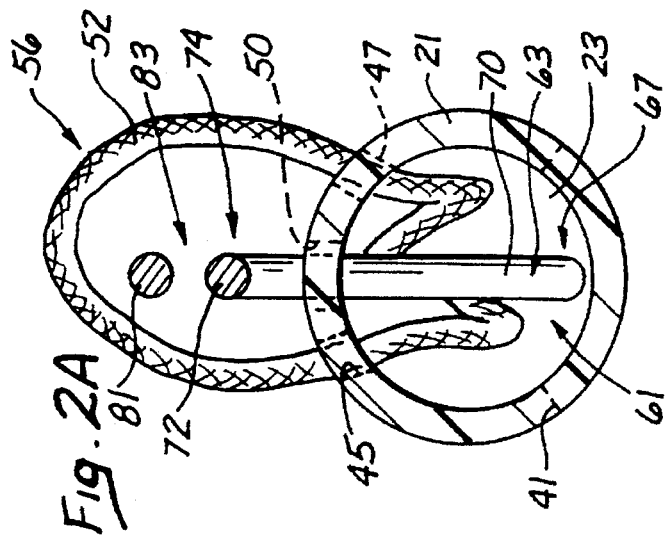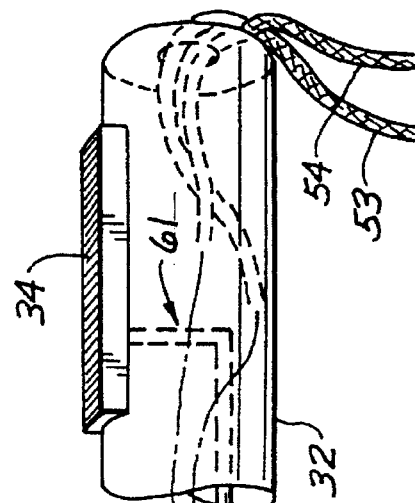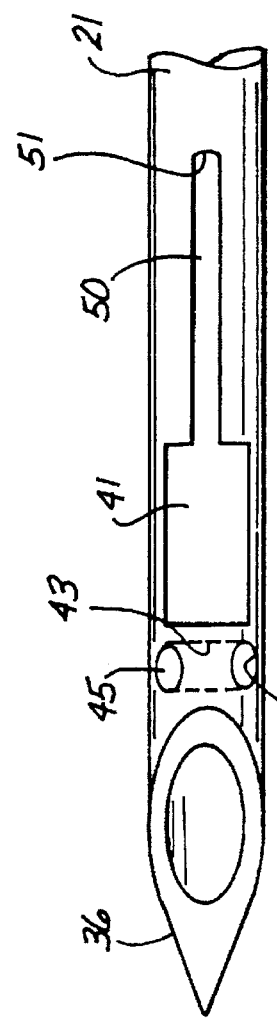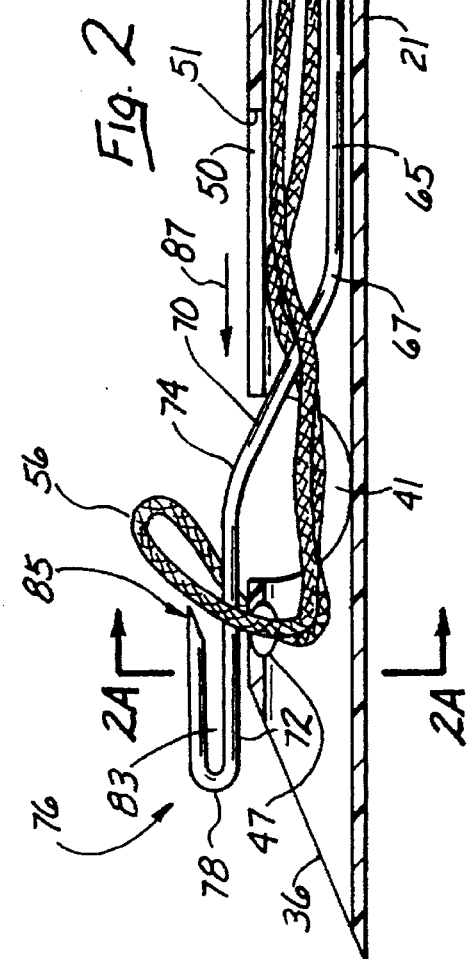

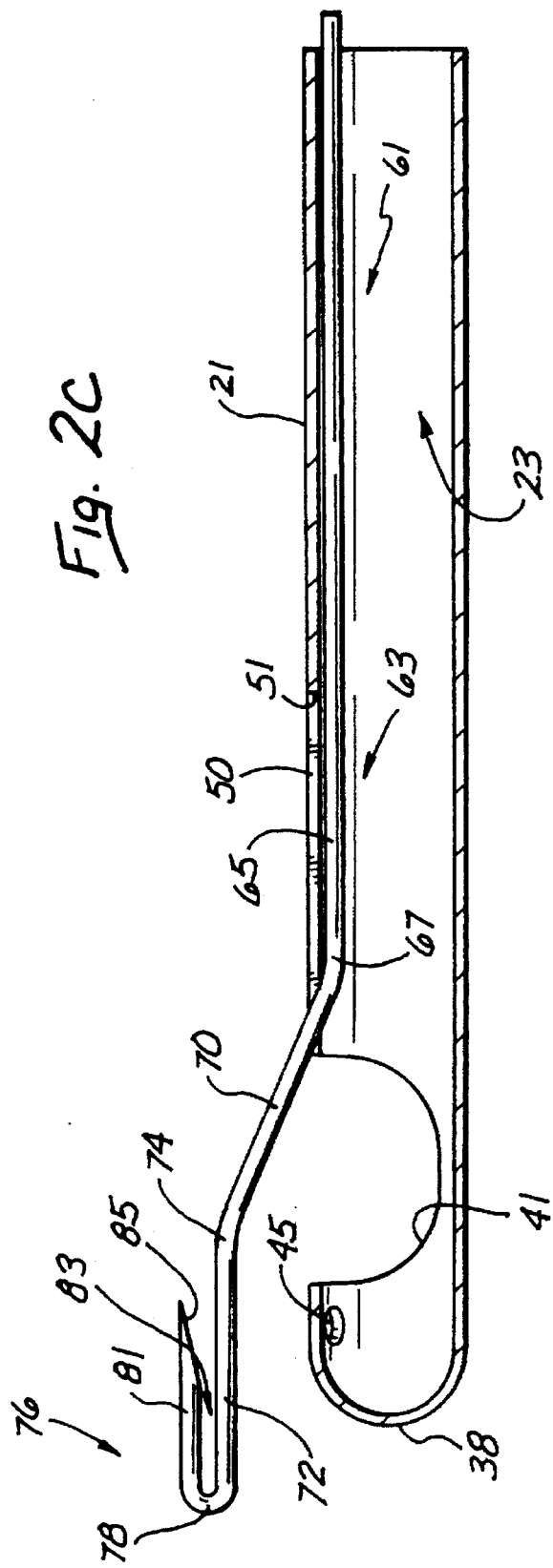
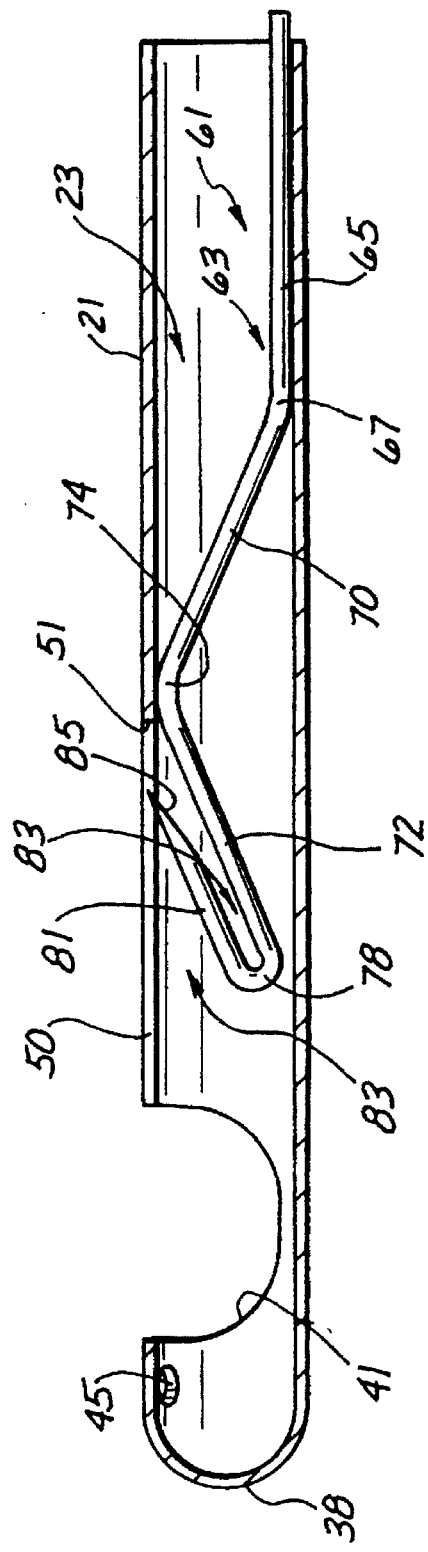

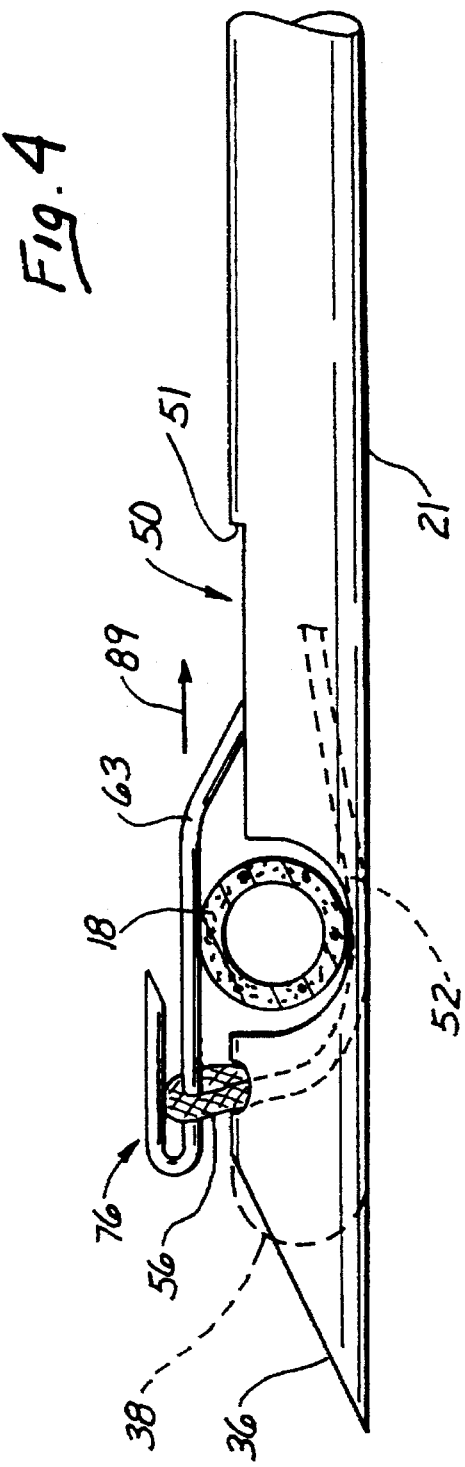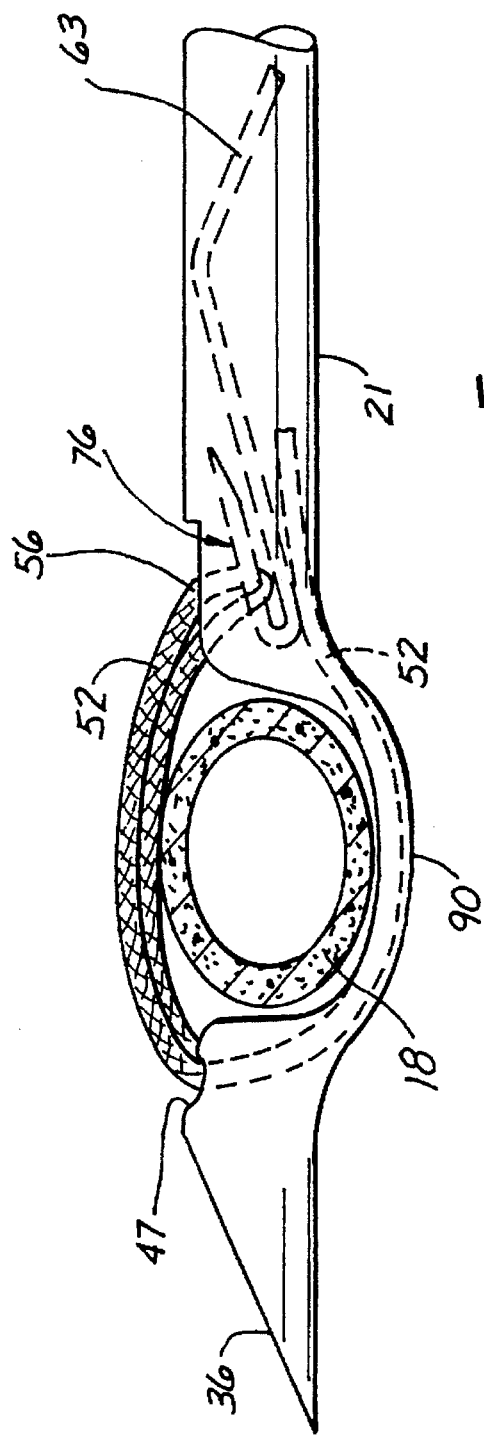

SURGICAL LIGATING DEVICE AND METHOD FOR USING SAME

BACKGROUND OF THE INVENTION

1. Field of the Invention

This invention relates generally to surgical instruments and devices, and more specifically to instruments for occluding, such as ligating, body conduits.

2. Discussion of the Prior Art

In many surgical applications, it is desirable to occlude body conduits such as blood vessels and other body ducts. Clips and clamps are commonly used for this purpose, but a procedure of particular interest employs a suture which circumscribes the conduit and is tied to itself to occlude the conduit. This procedure is referred to as ligation and is commonly used for the occlusion of blood vessels using a laparoscopic or percutaneous access device.

Although many devices of the prior art have tubular bodies and function to capture suture loops, they do not allow the operator to surround the vessel or duct without first cutting through it. Those device which do not require initial cutting are very complex, costly and generally require a large opening or port to permit insertion of the device. In addition, none of the devices of the prior art is adapted to be used in a truly percutaneous method without the use of a trocar or introducer sheath.

Ligation is also being used to engage and suspend a body conduit relative to a body wall. In this case it is desirable to leave the body conduit patent, but to direct it along a path defined by the ligation supports.

SUMMARY OF THE INVENTION

The present invention overcomes these deficiencies of the prior art. It includes a suture ligation device having an elongate tube with an axial channel extending between a distal end and a proximal end. At the proximal end a handle is provided with an actuator which is attached to a shaft or wire situated within the channel of the tube.

The distal end of the device is configured for placement in contact with the vessel or duct to be ligated. This distal end can be provided with a sharpened tip in order to facilitate percutaneous insertion of the device without the use of a trocar or introducer sheath. At the distal end, portions of the tube define a notch or recess which extends laterally from the channel of the tube. A suture extends from the proximal end of the tube through the channel and the notch and exits the tube through holes located distally of the notch. The distal end of this suture forms a suture loop or other engagable configuration.

An engagement apparatus, such as a hook, is formed at the distal end of the shaft. This engagement apparatus is initially carried within the channel of the tube to facilitate insertion of the device. However, it is movable by operation of the actuator and the attached shaft or wire, to a position exterior of the channel and distal of the recess.

In operation, the device is inserted percutaneously, or through a trocar or introducer sheath, into proximity with the conduit to be ligated. The device is positioned so that the conduit sits within the notch with the suture extending along the bottom of the notch. At this point, the actuator can be operated to deploy the wire or shaft and the associated engagement mechanism. Distal movement of the engagement mechanism causes the hook to deploy from the channel, over the top of the notch, to a position distal of the notch. When the proximal ends of the suture is pulled from the handle, the suture is drawn onto the wire or shaft of the engagement mechanism.

Subsequent proximal withdrawal of the shaft causes the hook to engage this suture loop and draw it over the notch and the conduit, back into the channel of the tube. Then the device can be manipulated to free the conduit from the notch and to withdraw from the body both ends of the suture. An appropriate slip knot can then be formed in the suture and slid or pushed back through the body wall to the operative site to complete the ligation of the conduit.

In one aspect of the invention, a ligating device includes an elongate tube having an interior channel and an axis extending between a proximal end an a distal end. A handle is disposed at the proximal end of the tube while portions of the tube at the distal end define a notch or recess extending into the channel transversely of the axis. A suture is positioned to extend along the channel and through the recess.

In another aspect of the invention, a ligating device includes an elongate tube having an interior channel and an axis extending between a proximal end and a distal end. A handle is disposed at the proximal end of the tube while portions of the tube at the distal end define a recess extending into the channel transversely of the axis. A suture extending through the channel includes first portions disposed proximally of the recess and second portions disposed distally of the recess. An engagement apparatus is movable by operation of the handle between a first position proximal of the recess and a second position distal of the recess. The second portions of the suture are engaged by the engaging apparatus in the second position to substantially encircle a conduit disposed in the recess and permit ligation of the conduit.

In yet another aspect of the invention, a method for ligating a conduit in a human body includes the steps of inserting the tube into the body, the tube having an axial channel, a transverse recess and a suture extending through the recess to regions exterior of the tube. The tube is positioned relative to the conduit so the conduit is disposed in the recess and over the suture. The method also includes the step of providing an engagement apparatus within the tube which is movable from the first proximal position to a second proximal position. Moving this engagement apparatus from the first position to the second position permits engagement of the suture in the regions exterior of the tube. Moving the engagement apparatus with the engaged suture from the second position to the first position permits withdrawal of the tube in the ends of the suture from the body. In this location, a slip knot can be tied in the suture and slid into ligating engagement with the conduit.

These and other features and advantages of the invention will become more apparent with a discussion of preferred embodiments and method steps, and reference to the associated drawings.

DESCRIPTION OF THE DRAWINGS

FIG. 2 is an axial cross-section view of a preferred embodiment of the ligating device showing a suture and an engagement apparatus in an extended state;

FIG. 2A is a radial cross-section view taken along lines 2a—2a of FIG. 2;

FIG. 2B is an axial cross-section view similar to FIG. 2 and illustrating the engagement mechanism in a stored state;

FIG. 2C is an axial cross-section view similar to FIG. 2b and illustrating the engagement apparatus in a deployed state;

FIG. 3 is a top plan view of the ligating device illustrated in FIG. 2;

FIG. 4 is a side elevation view of the embodiment shown in FIG. 2, illustrating operation of the engagement apparatus to encircle the conduit with a suture;

FIG. 5 is a side elevation view illustrating an embodiment preferred for ligating large body conduits;

FIG. 6 illustrates a step for manipulating the device to position the body conduit within a notch or recess of the device, and deploying an engagement apparatus to engage a suture having both proximal and distal ends;

FIG. 7 illustrates a step for circumscribing the conduit by withdrawing the distal end of the suture into the channel;

FIG. 8 illustrates a step for removing the ligating device and both the proximal and distal ends of the suture through the body wall;

FIG. 9 illustrates a step for tying a slip knot exteriorly of the body;

FIG. 10 illustrates a step for pushing the slip knot into proximity with the conduit to ligate the conduit; FIG. 12 illustrates a further method of the invention where the conduit is ligated at two axially spaced locations and severed there between.

DESCRIPTION OF PREFERRED EMBODIMENTS AND BEST MODE OF THE INVENTION

Figure 1:
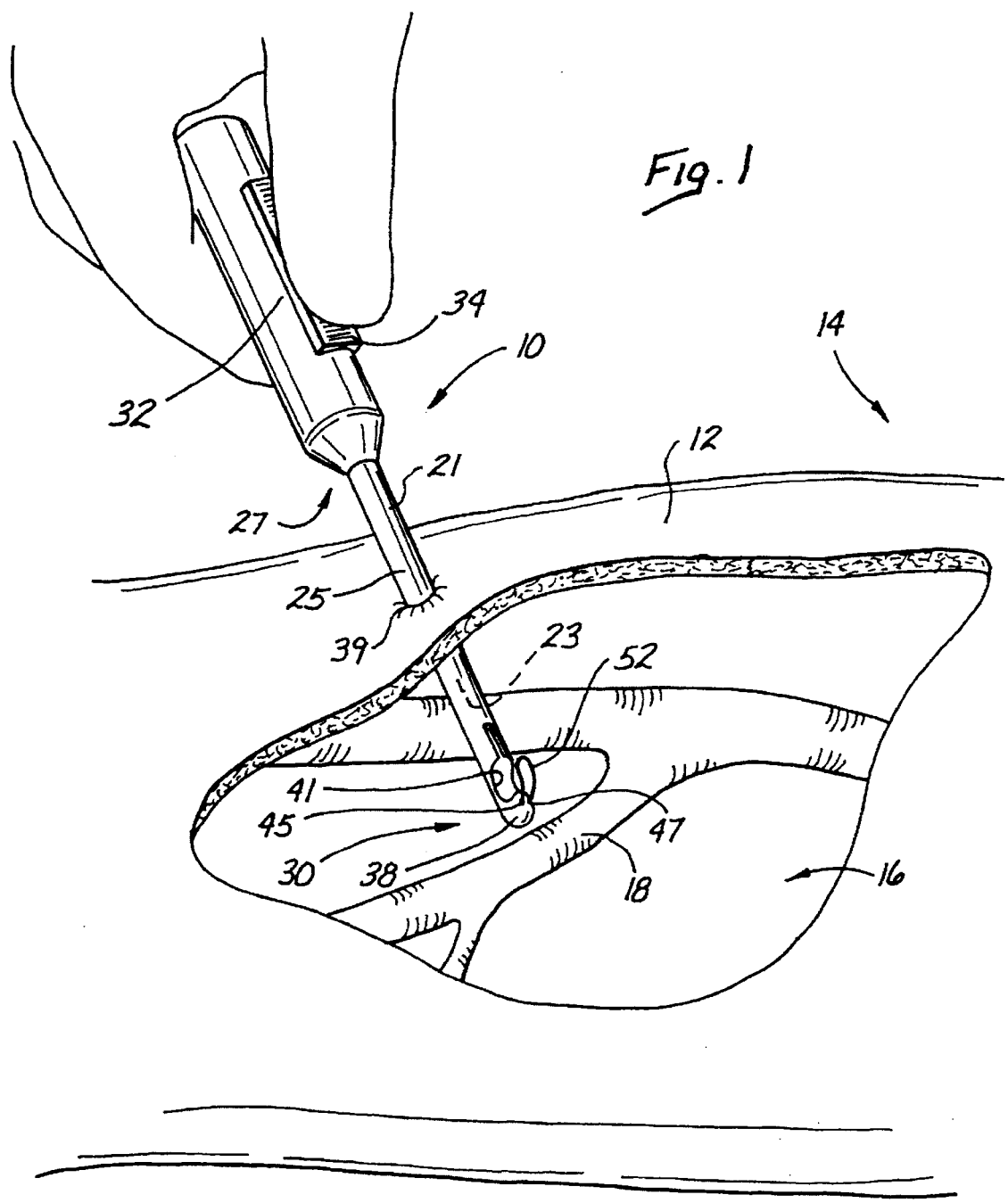
FIG. 1 is a perspective view of a human body with a ligating device of the present invention inserted percutaneously through a body wall to engage and ligate a conduit within the body.
Figure 6:
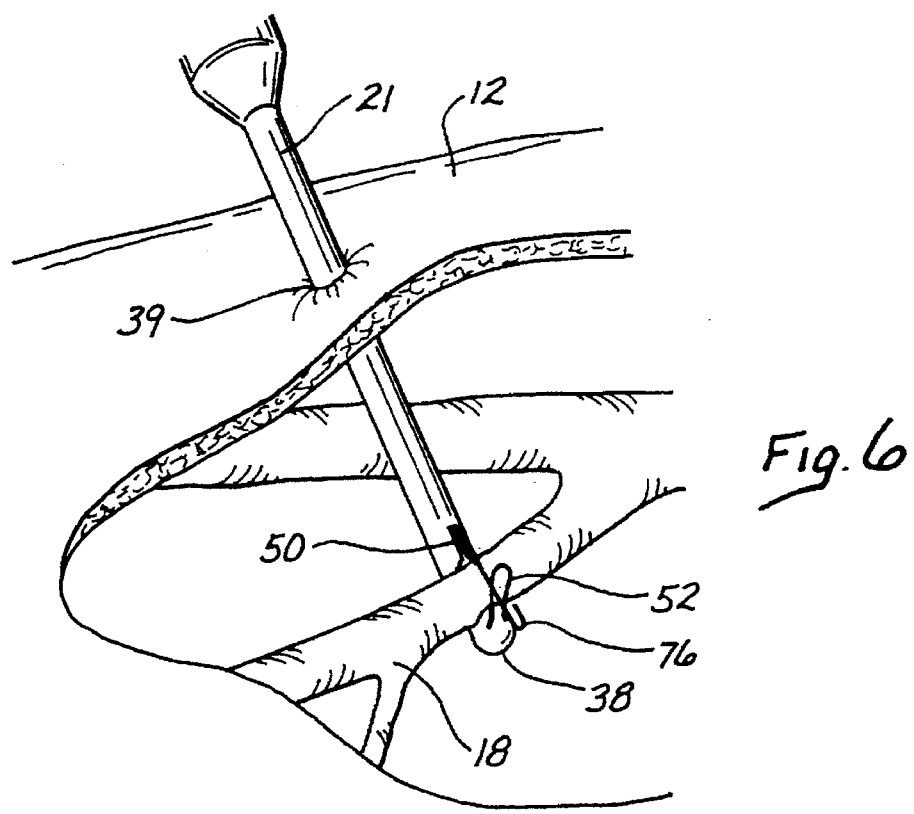
FIGS. 6–10 illustrate steps in a preferred method for ligating the body conduit.
Figure 7:
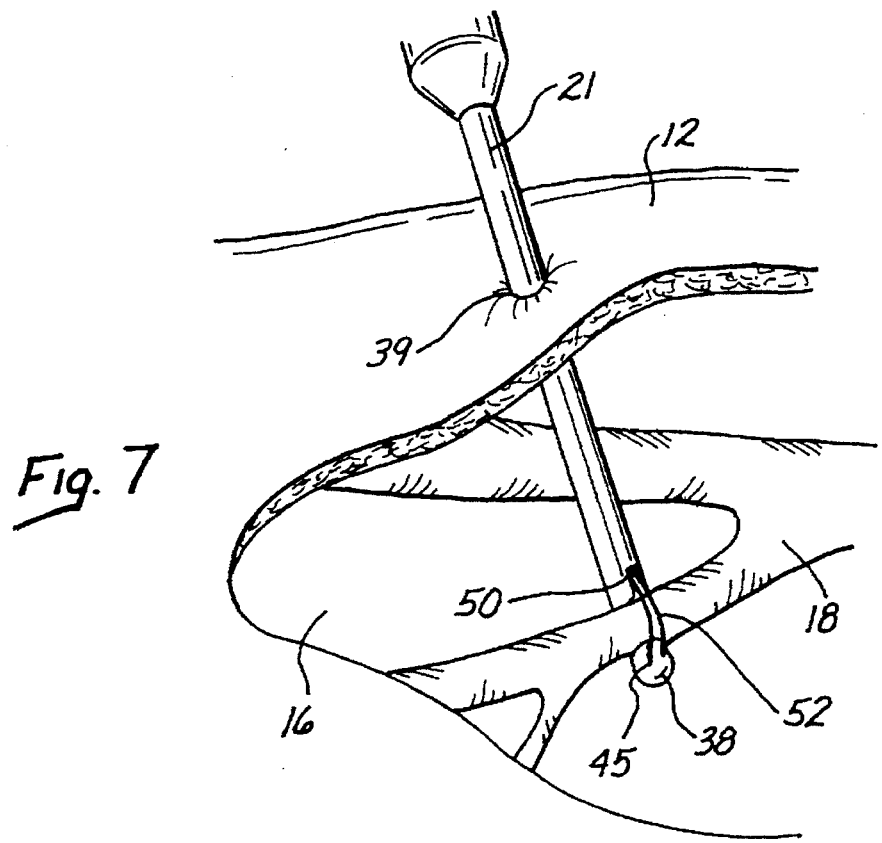
Figure 8:
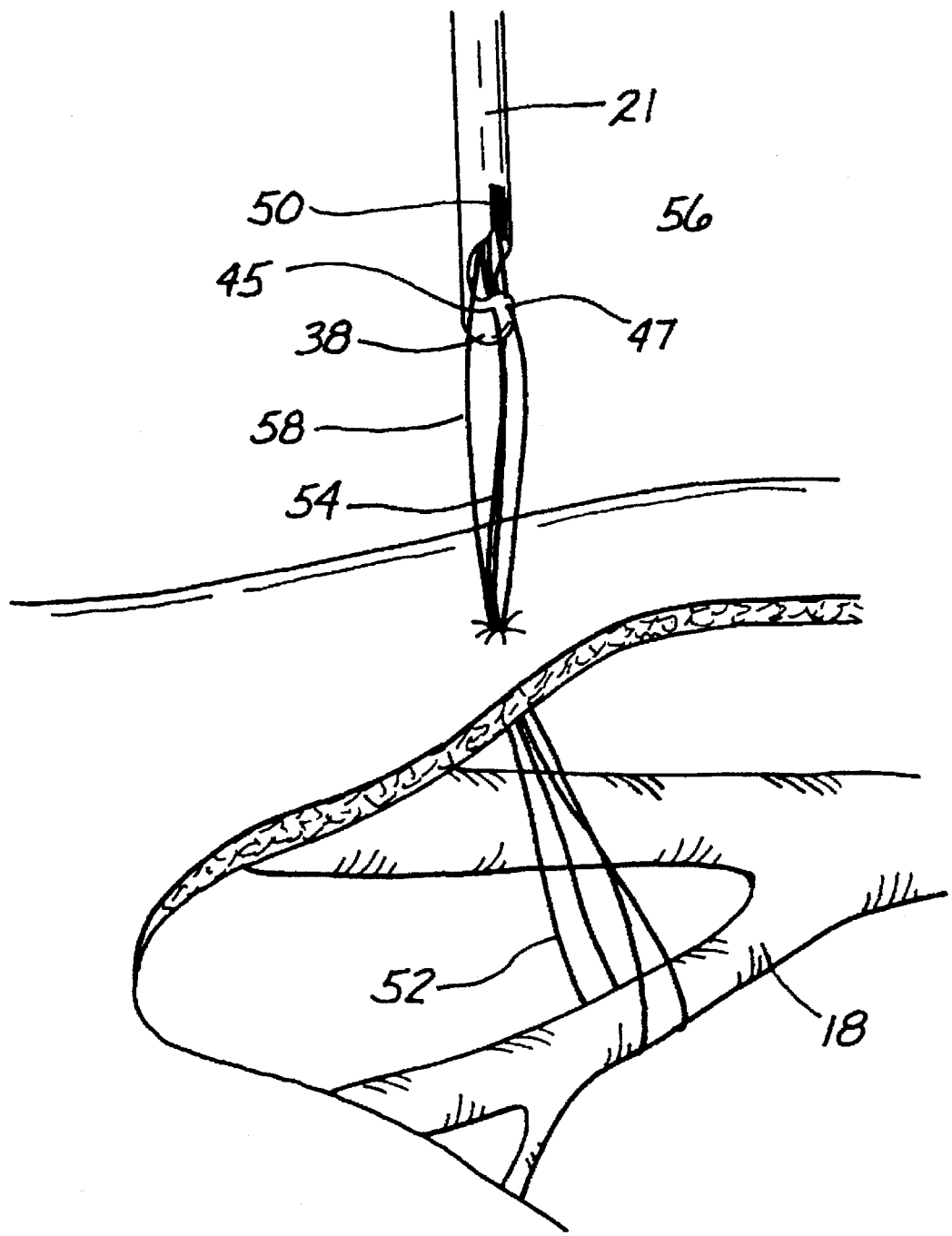

A surgical ligating device is illustrated in FIG. 1 and designated generally by the referenced numeral 10. The device 10 is illustrated in an operative disposition extending through an abdominal wall 12 of a body 14 and into an abdominal cavity 16. Within the cavity 16, the device 10 is operable to occlude, suspend, or otherwise ligate a body conduit such as a blood vessel 18. In the illustrated procedure, the device 10 is percutaneously inserted through the abdominal wall 12 without the aid of a trocar or other access device. Nevertheless, such access devices could be employed at the discretion of the surgeon.

An enlarged view of the surgical ligation device 10 is illustrated in the axial cross-section view of FIG. 2. In this embodiment, the device 10 includes an elongate tube 21 having a channel 23 extending along an axis 25 between a proximal end 27 and a distal end 30. A handle 32 is positioned at the proximal end 27 of the tube 21 and provided with a finger operable slide actuator 34, which is discussed in greater detail below.

At the distal end 30, the tube 21 can be provided with a sharp tip 36 (FIG. 2) facilitating percutaneous insertion of the device 10, or alternatively, a blunt tip 38 (FIG. 1) facilitating insertion of the device through a trocar or separate incision 39. The distal end 30 of the tube 21 is provided with a notch or recess 41 which extends laterally of the axis 25 in communication with the channel 23. This recess 41 is relatively large and preferably includes more than 180° of the circumference of the tube. In a preferred embodiment, the recess 41 includes about 240 degrees of the circumference of the tube 21 as illustrated in the radial cross-section view of FIG. 2A.

Between the tip 36 and the recess 41 the tube 21 can be provided with a lateral slot, shown by dotted lines 43 in FIG. 3 or preferably a pair of holes 45, 47 which are disposed laterally of each other. The tube 21 can also be provided with an axial slot 50 which extends proximally from the recess 41 to a camming shoulder 51. This slot 50 is positioned generally on the same side of the tube 21 as the recess 41 and the holes 45 and 47. In a preferred embodiment, the axial slot 50 bisects the recess 41 and a line drawn between the holes 45 and 47.

With the embodiment of FIG. 2, a suture 52 can be loaded into the device 10 prior to its use. The suture includes free ends 53 and 54 which are inserted respectively through the holes 45 and 47 and lead through the recess 41 and the channel 23 to exit the device at the proximal end of the handle 32. When the suture 52 is loaded in the manner, intermediate portions of the suture 52 form a suture loop 56 as it extends through the holes 45, 47 to regions exterior of the tube 21.

An engagement apparatus 61 associated with the actuator 34 includes a shaft or wire 63 which extends generally axially through the channel 23. At its proximal end, the wire 63 has a fixed relationship with the actuator 34 and consequently is movable generally axially within the channel 23 by operation of the actuator 34. Distally of the actuator 34, the wire 63 includes a first leg 65 which is connected through a bend 67 to a second leg 70. A third leg 72 is connected to the second leg 70 through a bend 74. At the distal end of the third leg 72, a hook 76 is formed where the wire or wire 63 is curled back on itself through a bend 78 to form a fourth leg 81. Between the third leg 72 and fourth leg 81, the hook 76 forms an engagement channel 83. A free end 85 of the fourth leg 81 can be beveled to form a funnel into the channel 83.

Operation of the actuator 34 and associated engagement apparatus 61 is best understood with reference to the axial cross-section views of FIGS. 2B and 2C. FIG. 2B illustrates the wire 63 in a first stored position wherein the wire 63 is disposed totally within the channel 23 of the tube 21. In a preferred embodiment, this position of the wire 63 is accompanied by the proximal-most position of the actuator 34, but also characterized by disposition of the bend 74 proximally of the camming shoulder 51 associated with the slot 50. With the wire 63 disposed in this first position illustrated in FIG. 2B, the first, second and third legs 65, 70 and 72, respectively, are all disposed generally transverse to the axis 25.

When the actuator 34 is moved to its ultimate distal position, the wire 63 is disposed at a second deployed position illustrated in FIG. 2. In this position, the hook 76 is disposed outside the channel 23 of the tube 21, with its free end 85 positioned slightly distally of the holes 45, 47. In the second position, the first leg 65 and third leg 72 can have a generally parallel orientation to the axis 25 while the second leg 70 extends through the slot 50 or recess 41 generally transverse to the axis 25.

Between the first proximal position of the wire 63, illustrated in FIG. 2B, and the second distal position of the wire 63 illustrated in FIG. 2, exists a third position of particular interest to operation of this engagement apparatus 61. This third position is best illustrated in FIG. 2C and occurs while the actuator 34 and the associated wire 63 are moved distally from the first, stored position. With this proximal movement, the wire 63 remains stored until the bend 74, between the second leg 70 and the third leg 72 clears the camming shoulder 51. At this point, the third leg 72 of the wire 63 swings upwardly and outwardly, as shown by the arrow 87, as the third leg 72 exits the slot 50. In this third intermediate position, the hook 76 will generally be disposed proximally of the recess 41. Further bending of the wire 63 will typically not occur as the actuator 34 is moved proximally and the engagement mechanism 61 moves from the third position illustrated in FIG. 2C to the second position illustrated in FIG. 2.

Operation of the surgical ligating device 10 will be better understood with consideration of the enlarged views of FIGS. 2 and 4, and reference to the perspective views of FIGS. 6–10. With the engagement apparatus 61 in its stored position, illustrated in FIG. 2B, and with the suture 52 mounted within the channel 23, as illustrated in FIG. 2, the device can be inserted through the abdominal wall 12 and manipulated to bring the recess 41 into juxtaposition with the vessel 18. In this operative position illustrated in FIG. 6, the suture 52 extends about 180° around the vessel 18. More specifically, the suture 52 extends along one side of the vessel 18 and beneath the vessel 18 as it exits through the holes 45, 47.

At this point, the engagement apparatus 61 can be deployed by distal movement of the actuator 34. This moves the engagement apparatus 61 from the first position illustrated in FIG. 2B to the third intermediate position illustrated in FIG. 2C.

When the engagement apparatus 61 is fully deployed, in the third position, it is desirable to capture the suture loop 56 within the channel 83 of the hook 76. In a preferred method, this is accomplished by pulling on the free ends 53, 54 of the suture 52 thereby drawing the suture loop 56 toward the holes 45, 47 and onto the third leg 72 of the wire 63.

With the suture loop 56 tightly held against the third leg 72, the engagement apparatus 61 can be withdrawn proximally by operation of the actuator 34. Initially this will move the suture loop 56 into the channel 83 formed by the hook 76. Further proximal movement of the actuator 34 and wire 63 will move the hook 76 and the captured suture loop 56 across the second side of the vessel 18 to substantially encircle the vessel 18 with the suture 52. This proximal withdrawal of the engagement apparatus 61 is best illustrated in FIG. 4 where further proximal movement of the wire 63 along an arrow 89 causes the suture 52 to substantially encircle the vessel 18 within the recess 41.

When the engagement apparatus 61, the camming shoulder 51 initially presses against the second leg 70 bending the third leg 72, the hook 76 and the captured suture loop 56 downwardly, in a direction opposite to the arrow 87 (FIG. 2), and into the channel 23 of the tube 21.

This final proximal movement of the engagement apparatus 61 results in storage of the hook 76 and engaged suture loop 56 within the channel 23. This disposition is illustrated in FIG. 5 where it can be seen that the vessel 18 is substantially encircled by the suture 52 but all elements of the engagement apparatus 61 are stored to facilitate withdrawal of the device 10. FIG. 5 also illustrated an embodiment of the invention wherein the tube 21 is provided with a bulge 90 along the outer surface. This bulge 90 can greatly increase the volume of the recess 41 thereby facilitating operation of the device 10 with respect to larger body ducts and conduits.

With the suture 52 substantially encircling the vessel 18, and with the engagement apparatus 61 stored within the channel 23, the device 10 can be removed from the operative site. This is accomplished by manipulating the handle 32 to free the vessel 18 from the recess 41 as the device 10 is withdrawn through the abdominal wall 12. In this step, both of the free ends 53, 54 as well as the suture loop 56 of the suture 52 are withdrawn through the abdominal wall, as illustrated in FIG. 9.

Figure 9:
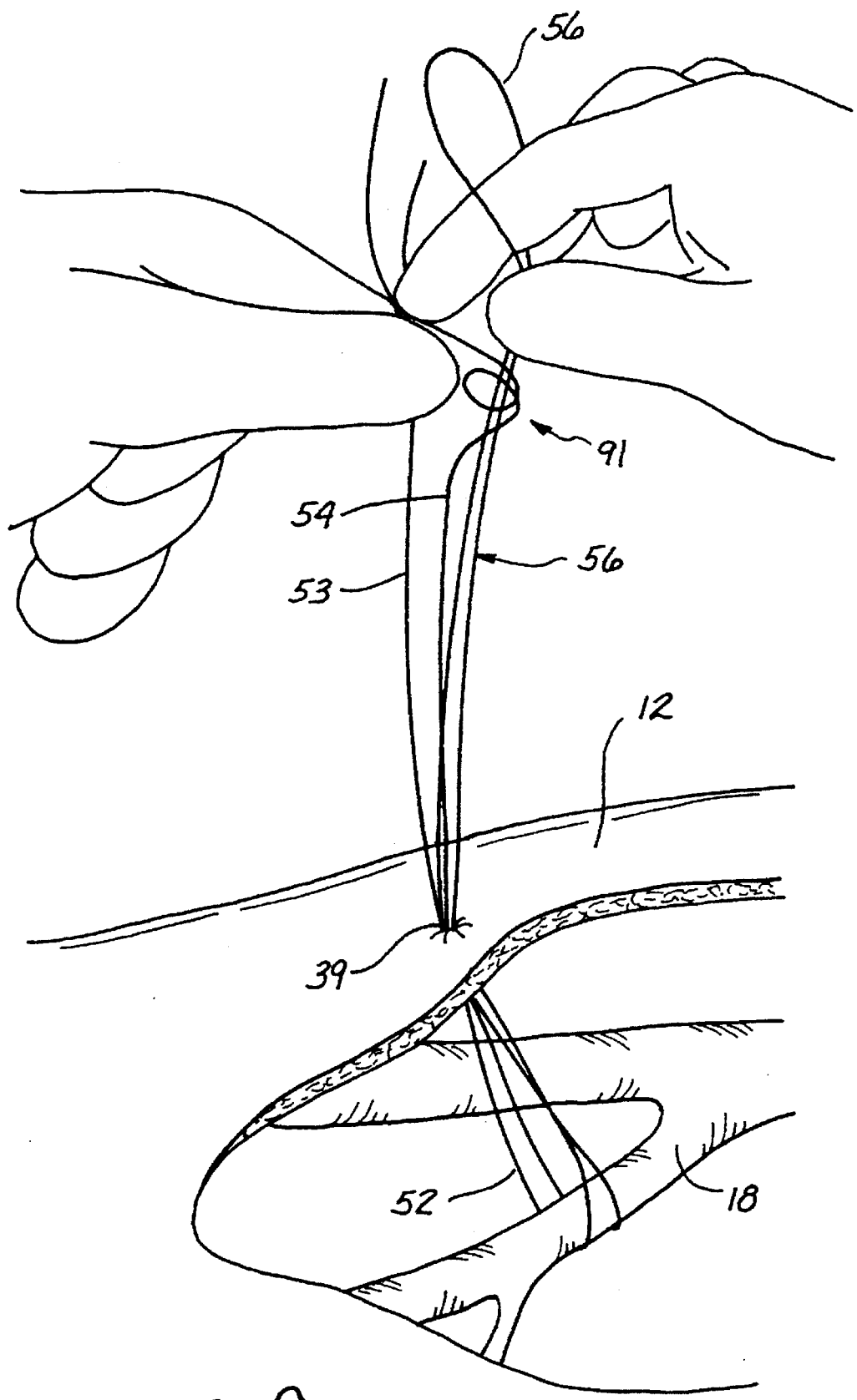
Figure 10:
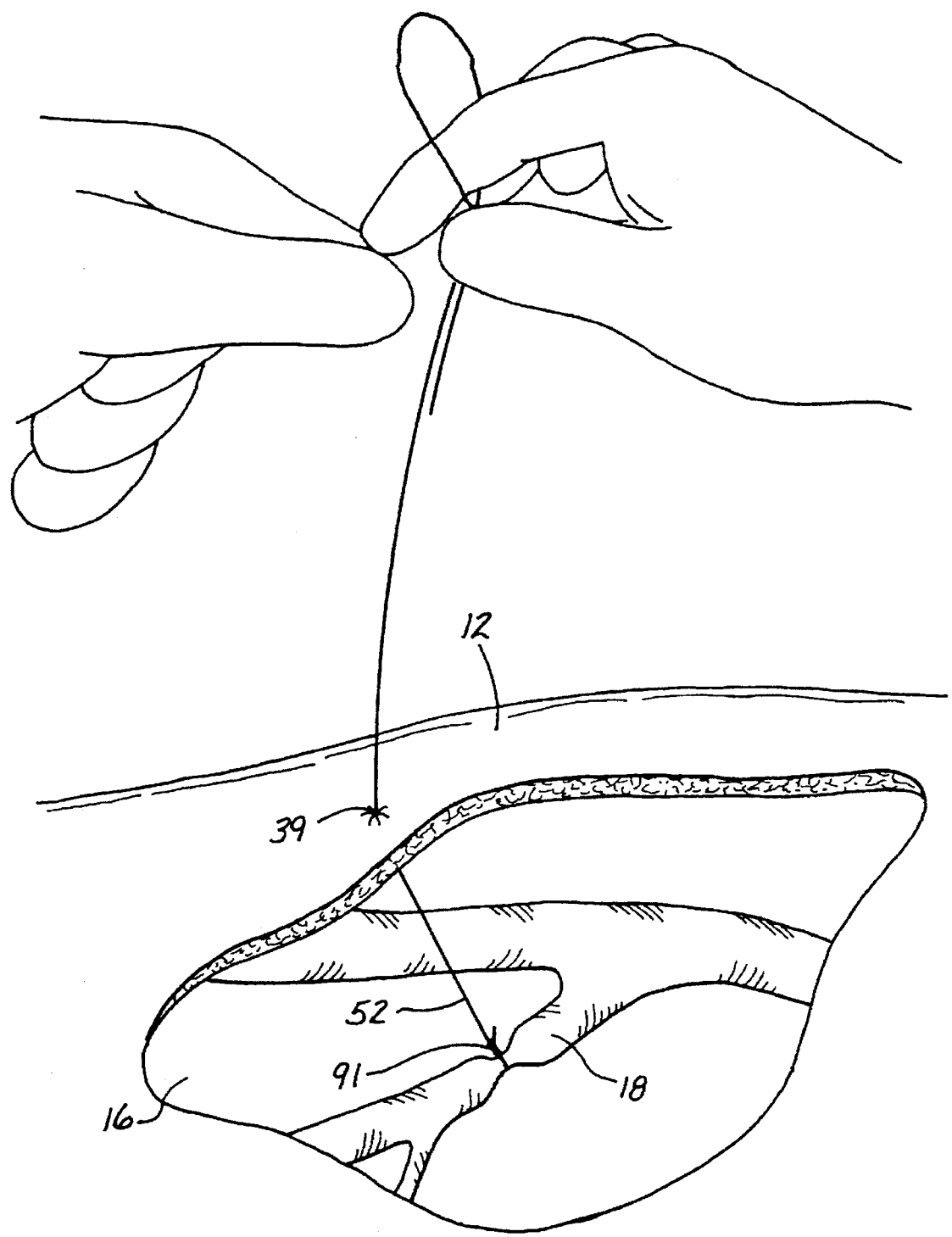

With further reference to FIG. 9, it will be noted that the foregoing method and apparatus leaves two strands of the suture 52 encircling the vessel 18 with the free ends 53, 54 and suture loop 56 extending on the opposite side of the abdominal wall 12. Given this configuration, there are many alternatives for finally ligating the vessel 18. If a single loop of ligating suture 52 is desired, one of the free ends, such as the free end 53, can be released and drawn from around the vessel 18 by pulling on the suture loop 56. A slip knot 91 can then be tied using the other free end, such as the end 54, and the knot slid into proximity to the vessel 18 as illustrated in FIG. 10.

Figure 11:
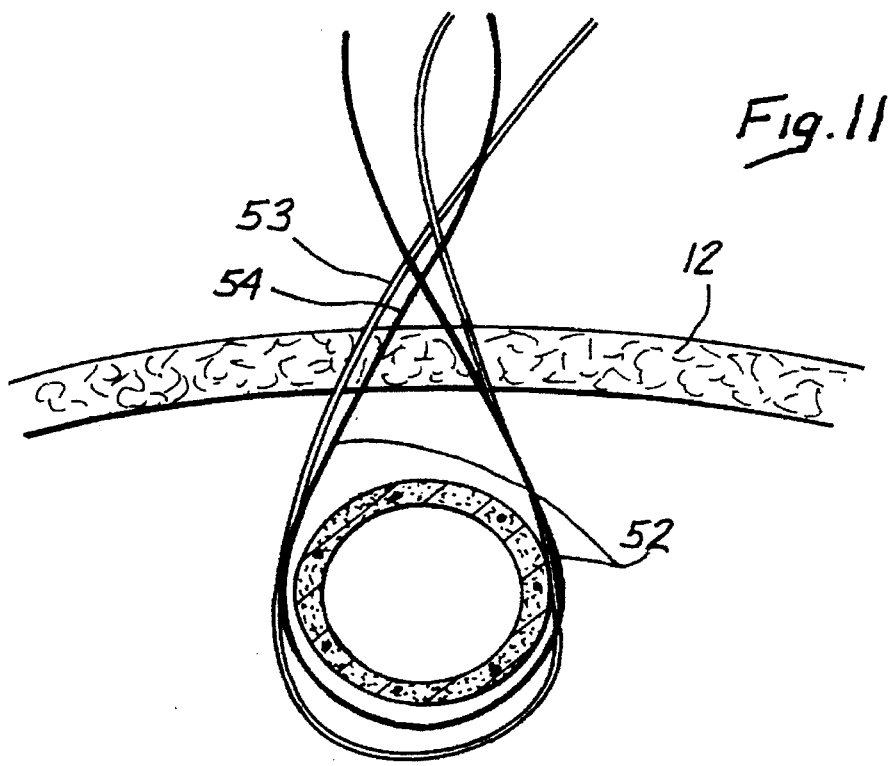
FIG. 11 illustrates an additional method of the invention where the conduit is ligated but not occluded to facilitate suspension of the conduit.

Suspension of the vessel 18 without occlusion is also an alternative. As illustrated in FIG. 11, the free ends 53, 54 and suture loop 56 can be withdrawn through the abdominal wall 12 in order to form a cradle 92 for the vessel 18. If the ends of the suture 52 are not pulled taunt, the vessel 18 will remain patent within the cradle 92.

Where two strands of the suture 52 are desired in order to reduce the pressure on the vessel 18, all four ends can be tied in either one or two slip knots 91 which can then be slid into proximity with the vessel 18. As a further alternative, one of the strands of the suture 52 can be used to occlude the vessel 18 while the other strand can be used to suspend the vessel 18.

Figure 12:
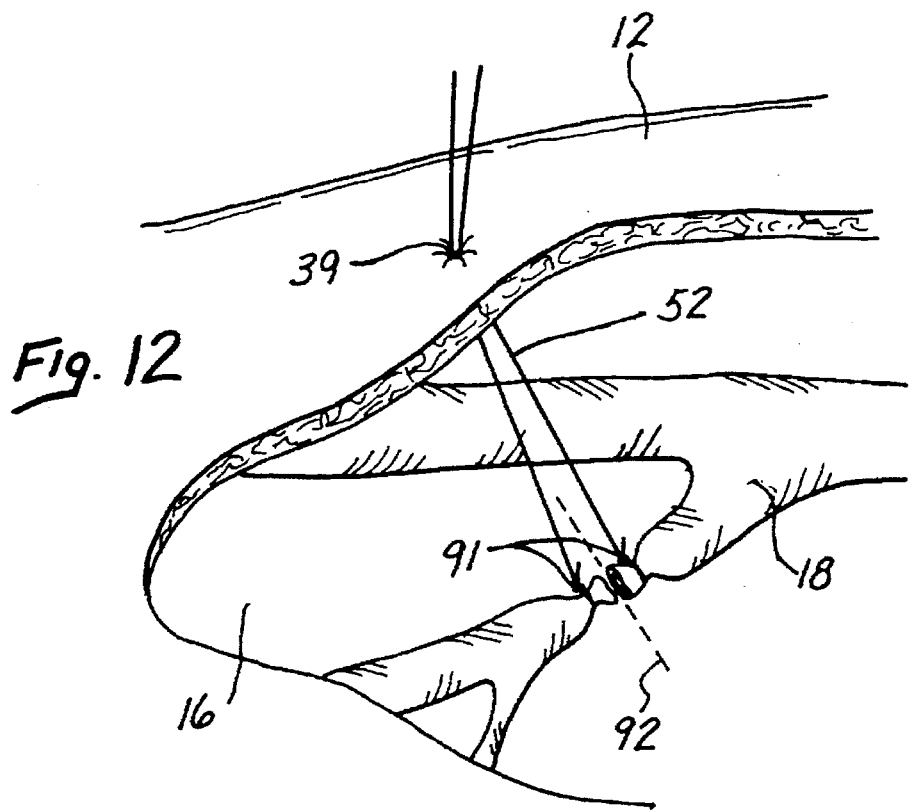

As an additional alternative, the two strands of the suture 52 can be individually tied to occlude the vessel 18 at two locations as illustrated in FIG. 12. Then, the vessel can be cut or otherewise severed between the two locations, for example along a dotted line 92 in FIG. 12.

Given these wide variations, which are all within the scope of this concept, one is cautioned not to restrict the invention to the embodiments which have been specifically disclosed and illustrated, but rather encouraged to determine the scope of the invention only with reference to the following claims.

I claim:

1. A method for ligating a conduit in a human body, comprising the steps of:

inserting a ligating device into the body, the device including a tube having an axial channel, a transverse recess in communication with the channel, a suture extending through the channel and outwardly through at least one hole in the tube distally from the recess to regions exterior of the tube, and an engagement apparatus movable from a first proximal position to a second distal position;

positioning the tube relative to the conduit so that the conduit is disposed in the transverse recess over the suture;

moving the engagement apparatus from the first position to the second position;

engaging the suture with the engagement apparatus;

moving the engagement apparatus with the engaged suture from the second position to the first position; and tying the suture around the conduit to ligate the conduit.

2. The method recited in claim 1 wherein the inserting step comprises the step of:

inserting an access device through the skin of the body; and inserting the tube through the access device.

3. The method recited in claim 1 wherein:

the inserting step includes the step of providing the engagement apparatus with characteristics for being moved from the first position within the channel to the second position exterior of the channel;

the first moving step includes the step of deploying the engagement apparatus from the first position to the second position; and the second moving step includes the step of advancing the engagement apparatus in the regions exterior of the channel to the second position.

4. The method recited in claim 3 wherein the engaging step includes the step of:

drawing the suture onto the engagement apparatus; and moving the engagement apparatus distally to engage the suture.

5. The method recited in claim 4 wherein:

the inserting step includes the step of forming the engagement apparatus with a hook having an opening facing distally; and the engaging step includes the step of drawing the suture onto the engagement apparatus proximally of the hook.

6. The method recited in claim 1 wherein following the second moving step and prior to the tying step, the method further comprises the step of:

withdrawing the tube from the body conduit with the engaged suture.

7. The method recited in claim 1 wherein the inserting step includes the steps of:

providing the tube with a sharp distal tip; and inserting the sharp distal tip of the tube through a body wall in order to insert the tube into the body.

8. The method recited in claim 1 wherein the inserting step includes the steps of:

cutting the body wall to form an incision; and moving the tube through the incision in the body wall to insert the tube into the body.

9. A ligating device, comprising:

an elongate tube having an interior axial channel extending between a proximal end and a distal end and a hole transverse to the channel adjacent the distal end;

a handle disposed at the proximal end of the tube;

portions of the tube defining a recess at the distal end proximally from the hole, the recess extending laterally of the axis and communicating with the channel;

a suture extending through the channel and including first portions disposed proximally of the recess and second portions disposed distally of the recess;

an engagement apparatus movable at the proximal end of the tube between a first position proximal of the recess and a second position distal of the recess; wherein the second portions of the suture are engageable by the engagement apparatus in the second position to substantially encircle a conduit disposed in the recess and permit ligation of the conduit.

10. The ligating device recited in claim 9 wherein the tube further comprises:

portions defining a sharp tip at the distal end of the tube to facilitate insertion of the tube through the skin of a patient.

11. The ligating device recited in claim 9 wherein the suture second portions of the suture include a suture loop.

12. The ligating device recited in claim 11 wherein the suture loop extends laterally of the axis of the tube.

13. The ligating device recited in claim 9 wherein the engaging apparatus includes:

a shaft having a distal end an a proximal end, at least the proximal end of the shaft being disposed within the channel of the tube; and a hook having a fixed relationship with the shaft at the distal end of the shaft and having an opening facing the proximal end of the shaft.

14. A method for ligating a conduit of a human body, comprising the steps of:

inserting a ligating device percutaneously into the body, the device including a tube having a channel extending from a proximal end to a distal end, a transverse recess at the distal end, a suture extending from the proximal end through the channel and the recess and exiting the tube through a hole in the tube distally from the recess, and an engagement apparatus movable at least partially across the recess from a first proximal position to a second distal position;

positioning the tube relative to the conduit with the conduit extending through the recess transverse to the channel such that the suture extends in juxtaposition to the conduit from a near side of the conduit to a far side of the conduit and through the hole in the tube to the exterior of the tube;

moving the engagement apparatus at least partially across the recess from the first position to the second;

engaging the suture with the engagement apparatus distally of the conduit;

moving the engagement apparatus with the engaged suture from the second position to the first position; and tying the suture around the conduit to ligate the conduit.

15. The method recited in claim 14 wherein:

the inserting step includes the step of forming the suture into a loop which extends outwardly from the tube through the hole and is operably positioned distally of the recess; and the engaging step includes the step of engaging the suture loop with the engagement apparatus distally of the recess.

16. The method recited in claim 15 wherein the forming step comprises:

forming the suture with two ends of the suture disposed at the proximal end and intermediate portions of the suture disposed between the proximal end and distal end and extending through the channel and through the recess and exiting the channel through the hole to form a loop of suture distally of the recess.

17. The method recited in claim 15 wherein the tying step comprises the steps of:

tying one of the suture ends to the suture loop to form a first ligating suture; and tying the other of the suture ends to the suture loop to form a second ligating suture.

18. The method recited in claim 14 wherein the step of engaging the suture comprises the steps of:

providing the engagement apparatus with a proximally facing hook; and engaging the suture with the hook distally of the recess.

19. A device for ligating a body conduit, comprising:

a tube having a channel extending along an axis between a proximal end and a distal end, and a hole in communication with the channel adjacent the distal end;

portions of the tube defining a recess at the distal end proximally from the hole, the recess extending laterally of the axis and communicating with the channel;

a handle disposed at the proximal end of the tube;

a suture extending through the channel from the proximal end of the tube through the hole to regions exterior of the tube;

an engagement apparatus movable outwardly of the recess from a first position proximal of the recess to a second position distal of the recess, the engagement apparatus in the second position engaging the suture distally of the recess;

the engaging apparatus being movable from the second position to the first position to draw the suture back across the recess; whereby a body conduit positioned in the recess is substantially encircled by the suture thereby facilitating ligation of the body conduit.

20. The device recited in claim 19 wherein the engagement apparatus includes:

a wire having a proximal end extending through the channel and a distal end with the configuration of a proximally facing hook.

21. The device recited in claim 19 wherein the engaging apparatus in the second position engages the suture exteriorly of the channel.

22. The device recited in claim 19 wherein the tube further comprises a second distal hole in communication with the channel and laterally spaced apart from the first hole and wherein the suture passes from inside the channel through both the first and second holes to regions exterior of the tube.

23. The device as recited in claim 19 wherein the hole comprises a slot and the slot is oriented generally laterally to the axis.

24. A device for ligating a body conduit disposed in a body cavity, comprising:

a tube insertable into the body cavity and having a channel extending between a proximal end and a distal end, the tube being positionable in the body cavity to receive the body conduit in a lateral recess of the tube;

the body conduit in the lateral recess of the tube having a proximal facing surface, a distally facing surface, an inner side, and an outer side;

a suture extending through the channel of the tube and along the inner side of the conduit when the conduit is in the recess of the tube and extending through at least one hole in the tube distally from the lateral recess to the exterior of the tube;

an engagement apparatus operable to extend from the channel of the tube outwardly through the recess and along the outer side of the conduit when the conduit is in the recess of the tube, to engage the suture distally of the conduit and to draw the suture back along the outer side of the conduit to substantially encircle the conduit in the recess of the tube;

whereby the suture can be tied around the conduit.

* * * * *